US012544253B2

(12) United States Patent
Church et al.

(10) Patent No.: US 12,544,253 B2
(45) Date of Patent: Feb. 10, 2026

(54) OSTOMY BAG DRAIN CAP AND METHOD OF USE

(71) Applicants: Pamela A Church, Sanbornville, NH (US); Emily J Thornton, Strafford, NH (US)

(72) Inventors: Pamela A Church, Sanbornville, NH (US); Emily J Thornton, Strafford, NH (US)

( * ) Notice: Subject to any disclaimer, the term of this patent is extended or adjusted under 35 U.S.C. 154(b) by 0 days.

(21) Appl. No.: 19/246,507

(22) Filed: Jun. 23, 2025

(65) Prior Publication Data

US 2026/0000532 A1 Jan. 1, 2026

Related U.S. Application Data

(60) Provisional application No. 63/664,704, filed on Jun. 26, 2024.

(51) Int. Cl.

| | |
|---|---|
| ***A61F 5/448*** | (2006.01) |
| ***A61F 5/445*** | (2006.01) |
| *A61F 5/44* | (2006.01) |

(52) U.S. Cl.
CPC ............ *A61F 5/448* (2013.01); *A61F 5/4407* (2013.01); *A61F 5/445* (2013.01)

(58) Field of Classification Search
CPC ......... A61F 5/448; A61F 5/445; A61F 5/4407
See application file for complete search history.

(56) References Cited

U.S. PATENT DOCUMENTS

| | | | | |
|---|---|---|---|---|
| 2,154,202 A * | 4/1939 | Gricks | A61F 5/445 604/334 |
| 4,519,797 A * | 5/1985 | Hall | A61F 5/445 604/339 |
| 6,116,780 A * | 9/2000 | Young | A47K 11/02 383/44 |
| 7,468,056 B2 | 12/2008 | Burt | |
| 8,317,763 B2 * | 11/2012 | Tapia | A61F 5/445 604/335 |

(Continued)

FOREIGN PATENT DOCUMENTS

EP 3 544 554 B1 4/2024

OTHER PUBLICATIONS https://tinyurl.com/35j8wkhz; Ostomy Care Product Catalogue; Oct. 20, 2025.

*Primary Examiner* — Guy K Townsend
(74) *Attorney, Agent, or Firm* — The Inventor's Friend Patent Law Firm, P.L.L.C.; Nathaniel A. Wickliffe

(57) ABSTRACT

Embodiments of the present disclosure relates to a drain cap for an ostomy bag. The drain cap may be a rectangular pocket shaped structure configured to fit over drainage end of an ostomy bag and prevent accidental openings and provide enhanced user comfort. The pocket may be formed from a fabric having two layers of polyester-spandex and a layer of neoprene sandwiched between the two layers of polyester-spandex. The fabric may provide sufficient elasticity to secure the pocket in place during use. Further, the fabric may provide sufficient thickness to provide cushioning against the drainage end of the ostomy bag preventing skin irritation caused by contact with sharp and rigid edges. The drain cap may slip on easily, stays securely in place due to its bi-directional stretch, and protects the skin from irritation caused by sharp edges.

18 Claims, 16 Drawing Sheets

(56) References Cited

U.S. PATENT DOCUMENTS

| | | | | |
|---|---|---|---|---|
| 8,343,119 | B2 | 1/2013 | Mayer | |
| 8,475,420 | B2 * | 7/2013 | Hansen | A61F 5/4407 604/327 |
| 8,905,987 | B2 * | 12/2014 | Murray | A61F 5/445 383/57 |
| 9,668,910 | B2 * | 6/2017 | Murray | A61F 5/4407 |
| 2010/0152686 | A1 * | 6/2010 | Ryder | A61F 5/445 604/332 |
| 2011/0028923 | A1 * | 2/2011 | Murray | A61F 5/4405 604/332 |
| 2011/0028924 | A1 * | 2/2011 | Murray | A61F 5/4407 604/332 |

* cited by examiner

OSTOMY BAG DRAIN CAP AND METHOD OF USE

RELATED APPLICATIONS

This application claims the benefit of U.S. Provisional Application Ser. No. 63/664,704, entitled OSTOMY BAG DRAIN CAP, and filed Jun. 26, 2024, the entire disclosure of each of which is herein incorporated by reference.

FIELD OF THE INVENTION

The present disclosure relates to medical devices, and in particular, relates to a drain cap for ostomy bag.

BACKGROUND OF THE INVENTION

Ostomy bags are essential devices for individuals undergoing surgeries that necessitate external waste collection, such as colostomies, ileostomies, or urostomies. These devices have become indispensable for improving the quality of life for patients, allowing them to manage waste disposal efficiently and hygienically. However, the design of ostomy bag drainage ends has long posed challenges.

Conventional drainage mechanisms often include simple closure tabs, clips, or Velcro-based fasteners, which, while functional, are prone to failure under certain conditions. Accidental openings can result in spillage, leading to embarrassment, hygiene concerns, and damage to the user's clothing or surroundings. This is particularly concerning for active individuals or those who rely on their ostomy bags during extended periods without immediate access to a restroom.

Existing solutions to secure the drainage end include rigid covers or clamp-based mechanisms. While these designs address the issue of accidental openings to some extent, they introduce new concerns. Rigid materials can be uncomfortable against the user's body, especially when worn for extended durations. Furthermore, the lack of adaptability in such designs limits their compatibility with various shapes and sizes of drainage ends.

In addition to security concerns, the edges of drainage tabs or seals often cause skin irritation, particularly when they press against the user's body during movement. Some prior art attempts to address this issue with adhesive padding or fabric overlays. However, these solutions either lack durability or fail to provide adequate cushioning, making them unsuitable for prolonged use.

Another significant drawback of existing designs is their lack of reusability. Many options are disposable, which increases the financial burden on users and contributes to environmental waste. Even reusable options often lack the durability or ease of cleaning required for long-term use. Therefore, there is a need for a protective cap for the drainage end of an ostomy bag to securely prevent leaks, and protect the user's skin.

SUMMARY OF THE INVENTION

This disclosure overcomes disadvantages of the prior art by providing a system and method of use for a drain cap designed to fit over the drainage end of an ostomy bag. The cap may be a rectangular pocket shaped structure, constructed from a fabric having two layers of polyester-spandex with a neoprene core in-between, providing elasticity for secure placement and cushioning to prevent skin irritation from sharp edges. The cap may be applied by stretching it over the drainage end and remains in place due to its original shape, while removal involves reversing this process. The polyester spandex layer may be composed of approximately 90% polyester and approximately 10% spandex with a thickness of approximately 1.5 mm, ensuring bidirectional stretch and durability. The pocket may be manufactured by cutting and folding the fabric, sewing the sides with polyester-wrapped core-spun thread, and finishing with either a straight or decorative edge. Reusable and washable, the cap may be made using various techniques, including sewing, gluing, heat pressing, or extruding.

An embodiment of present disclosure relate to an ostomy bag drain cap. The drain cap may include a rectangular pocket shaped structure configured to fit over drainage end of an ostomy bag. The pocket may be formed from a fabric including two layers of polyester-spandex and a layer of neoprene sandwiched between the two layers of polyester-spandex. The pocket may be formed by cutting the fabric into a rectangular piece, folding the piece in half, and securing the sides with ⅛" seam allowances. The pocket may be configured to fit over the drainage end of the ostomy bag by way of sliding on in a stretched form, such that the pocket stays in place in an original form. Moreover, the pocket may be removed from the drainage end of the ostomy bag by way of stretching and sliding back. Additionally, the pocket may be manufactured using sewing, gluing, heat pressing, and/or extruding. Also, the pocket may be configured to be reusable and washable. In an embodiment, top edge of the pocket may be straight and/or cut.

In an embodiment, the fabric may provide sufficient elasticity to secure the pocket in place during use. Further, the fabric may have a thickness to provide cushioning against the drainage end of the ostomy bag preventing skin irritation caused by contact with sharp and rigid edges. Further, the fabric may include approximately 90% polyester and approximately 10% spandex. The fabric may have a thickness of approximately 1.5 mm. The fabric may be stretchable in both lengthwise and widthwise directions to ensure secure attachment to the drainage end of the ostomy bag. In an embodiment, seams of the drain cap may be sewn using polyester wrapped core-spun thread.

An ostomy bag drain cap can have a pocket configured to fit over a rolled drainage end of an ostomy bag. The pocket can have a front panel made from a layered fabric, a back panel made from the layered fabric, and an opening at a top of the pocket adapted to allow the rolled drainage end to be inserted into the pocket. The fabric can include an outer layer of 4-way stretchable fabric adapted to provide elasticity and to secure the pocket around a rolled drainage end during use, and a padding layer of compressible and resilient fabric inside of the outer layer of 4-way stretchable fabric, the padding layer providing body and providing cushioning around the drainage end to prevent skin irritation caused by contact with the rolled drainage end.

In various embodiments, the layered fabric may include an inner layer of 4-way stretchable fabric adapted to provide elasticity and to secure the pocket around the rolled drainage end during use, wherein the padding layer is sandwiched between the inner layer and the outer layer. The outer layer of 4-way stretchable fabric may include approximately 90% polyester and approximately 10% spandex. The padding layer of compressible and resilient fabric may include neoprene. The layered fabric may have a combined thickness in a range between approximately 1 mm and approximately 2 mm. The drain cap can include an elasticized retention band encircling the opening of the pocket. The drain cap can include side seams that connect the front panel and the back panel along the sides of the pocket so that the side seams are adapted to align with the sides of the rolled drainage end.

An ostomy sanitation system may include an ostomy bag and a drain cap. The ostomy bag may include a pouch for storage of waste materials and drainage end with a chute configured to be closed by rolling the end of the end chute to create a rolled seal. The drain cap may include a pocket configured to fit over the drainage end of an ostomy bag when the drainage end is rolled, and the pocket may have a front panel made from a layered fabric, a back panel made from the layered fabric, and an opening at a top of the pocket adapted to allow the rolled drainage end to be inserted into the pocket. The layered fabric may include an outer layer of 4-way stretchable fabric adapted to provide elasticity and to secure the pocket around a rolled drainage end during use and a padding layer of compressible and resilient fabric inside of the outer layer of 4-way stretchable fabric, the padding layer providing body and providing cushioning around the drainage end to prevent skin irritation caused by contact with the rolled drainage end.

A method of securing an ostomy bag drain end can include rolling or folding the ostomy bad drain end into a rolled conformation in order to seal the ostomy bag drain end, and stretching the opening of an ostomy bag drain cap, the drain cap having a pocket configured to fit over a rolled drainage end of an ostomy bag, the pocket having a front panel made from a layered fabric and a back panel made from the layered fabric, and an opening at a top of the pocket adapted to allow the rolled drainage end to be inserted into the pocket, wherein the layered fabric may have an outer layer of 4-way stretchable fabric adapted to provide elasticity and to secure the pocket around a rolled drainage end during use and a padding layer of compressible and resilient fabric inside of the outer layer of 4-way stretchable fabric, the padding layer providing body and providing cushioning around the drainage end to prevent skin irritation caused by contact with the rolled drainage end. The method can include placing the ostomy cap around the rolled end, and releasing the stretched drain cap so that the outer layer of 4-way stretchable fabric contracts around the rolled drainage end.

In various embodiments, placing the ostomy cap around the rolled end can include aligning side seams of the pocket to abut the sides of the rolled drainage end. Releasing the stretched drain cap can include releasing a stretched retention band so that the rolled drainage end is within the pocket and the retention band retains the rolled drainage end within the pocket. The method may include removing the drain cap, washing the drain cap, and reusing the drain cap.

The features and advantages of the subject matter here will become more apparent in light of the following detailed description of selected embodiments, as illustrated in the accompanying figures. As will be realized, the subject matter disclosed is capable of modifications in various respects, all without departing from the scope of the subject matter. Accordingly, the drawings and the description are to be regarded as illustrative in nature.

BRIEF DESCRIPTION OF THE DRAWINGS

The present subject matter will now be described in detail with reference to the drawings, which are provided as illustrative examples of the subject matter so as to enable those skilled in the art to practice the subject matter. Notably, the figures and examples are not meant to limit the scope of the present subject matter to a single embodiment, but other embodiments are possible by way of interchange of some or all of the described or illustrated elements and, further, wherein.

Figure 1A:
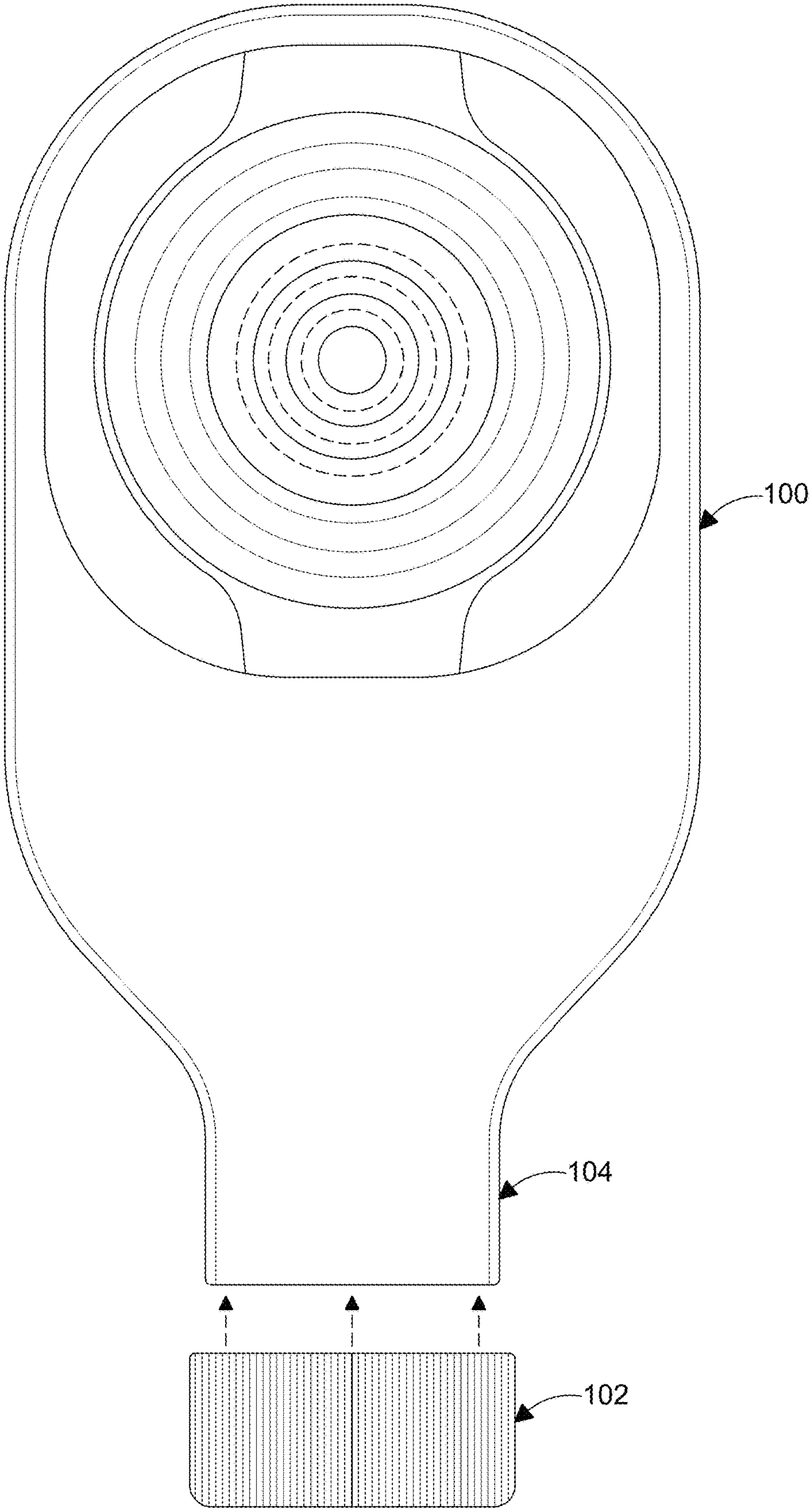
FIG. 1A is a top view of an open ostomy bag with an unrolled drainage end and a drain cap positioned to be placed over the drainage end, according to an illustrative embodiment.

Other features of embodiments of the present disclosure will be apparent from accompanying drawings and detailed description that follows.

DETAILED DESCRIPTION

In the following description, for purposes of explanation, numerous specific details are set forth in order to provide a thorough understanding of the present disclosure. It will be apparent, however, to one skilled in the art that the present disclosure is not limited to these specific details. In other instances, structures and devices are shown in block diagram form only in order to avoid obscuring the present technology.

The terms “connected” or “coupled” and related terms are used in an operational sense and are not necessarily limited to a direct connection or coupling. Thus, for example, two devices may be coupled directly, or via one or more intermediary media or devices. As another example, devices may be coupled in such a way that information can be passed there between, while not sharing any physical connection. Based on the disclosure provided herein, one of ordinary skill in the art will appreciate a variety of ways in which connection or coupling exists in accordance with the aforementioned definition.

If the specification states a component or feature “may”, “can”, “could”, or “might” be included or have a characteristic, that particular component or feature is not required to be included or have the characteristic.

Reference in this specification to “one embodiment” or “an embodiment” means that a particular feature, structure, or characteristic described in connection with the embodiment is included in at least one embodiment of the present disclosure. The appearance of the phrase “in one embodiment” in various places in the specification are not necessarily all referring to the same embodiment, nor are separate or alternative embodiments mutually exclusive of other embodiments. Further, the terms “a” and “an” herein do not denote a limitation of quantity, but rather denote the presence of at least one of the referenced items. Moreover, various features are described which may be exhibited by some embodiments and not by others. Similarly, various requirements may be described which may be requirements for some embodiments but not for other embodiments.

Embodiments of the present disclosure relate to a drain cap for an ostomy bag to provide a secure, comfortable, and reusable solution for users. The cap prevents accidental openings, thereby ensuring the secure containment of waste and improving hygiene. Further, the cap can include a stretchable, multilayered fabric structure, which can include outer layers made from a polyester-spandex blend for elasticity and durability, and an inner cushioning layer of neoprene for added comfort and protection. This layered combination of materials allows the cap to securely fit over the drainage end of an ostomy bag without the need for additional fasteners, ensuring ease of use and convenience. Furthermore, the cap also offers protection against skin irritation caused by the sharp edges of the drainage end, which is a common issue with conventional designs.

In one embodiment, the cap is fabricated by folding and stitching a rectangular fabric piece to form a pocket-like structure. In various embodiments, the edges of the cap may be finished with pinking shears for aesthetic purposes. Further, the cap is washable and reusable, making it both cost-effective and environmentally friendly. Additionally, flexibility of the cap ensures that it can be easily applied, removed, and cleaned by users of varying abilities. Also, the cap may accommodate various sizes and shapes of drainage ends, providing a versatile and adaptable solution for different ostomy bag types.

By integrating functionality, comfort, and reusability, embodiments of the present disclosure offer an improved alternative to conventional ostomy bag drainage end solutions. The cap addresses key issues such as leakage, skin irritation, and security while providing an accessible and reliable solution for users. Furthermore, the cap not only provides a multitude of benefits, but also the simple design can be manufactured at very low costs, and allows for repeated washings and reuses.

Figure 1B:
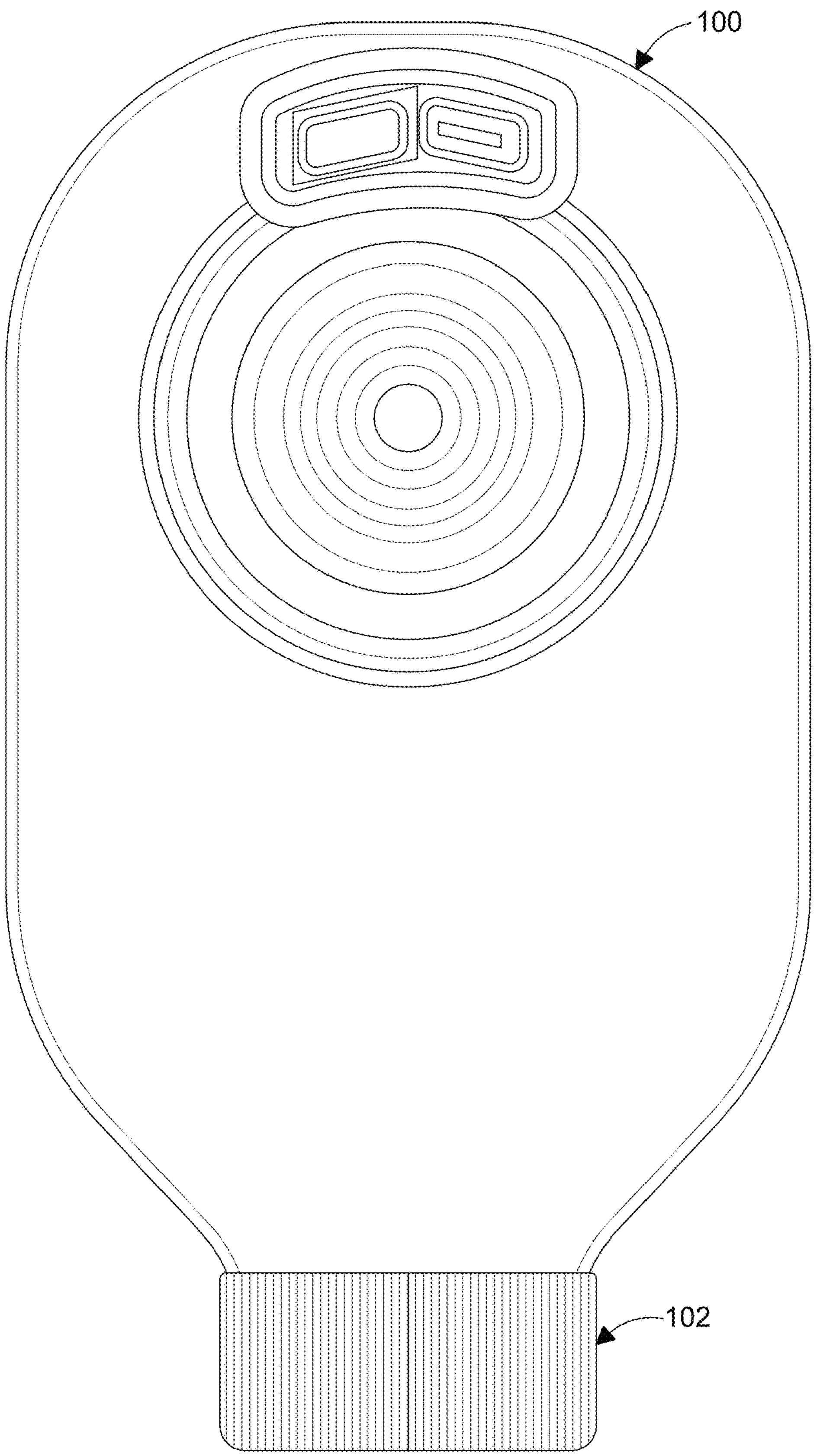
FIG. 1B is a top view an ostomy bag with a drain cap placed over the drainage end 104 according to an illustrative embodiment.

FIG. 1A is a top view of an open ostomy bag 100 with an unrolled drainage end 104 and a drain cap 102 positioned to be placed over the drainage end, according to an illustrative embodiment, and FIG. 1B is a top view an ostomy bag 100 with a drain cap 102 placed over the drainage end 104, according to an illustrative embodiment. For the sake of brevity FIG. 1A and FIG. 1B will be explained together.

In an embodiment, the ostomy bag 100 may include the drainage end 104 for emptying the contents of the bag. The drainage end 104 can be unrolled, as shown in FIG. 1A, allowing the contents of the bag to be emptied. The drainage end 104 is designed to be rolled up, or put another way, the drainage end is designed to be folded over itself several times, to create a seal at the end of the ostomy bag. Rolling or folding the end of the drainage end can close the drainage end of the ostomy bag. However, the ostomy bag is often constructed of a strong plastic material, and the rolled or folded drainage end may have rigid or pointy corners or edges that can be uncomfortable to the user. Furthermore, the drainage end may come unfastened or unfolded, resulting in unintended leakage. A soft, flexible, and padded drain cap 102 can be placed over the end of the drainage end 104 to improve user comfort and secure the drainage end in a rolled and closed conformation.

The drain cap 102 may be a rectangular, pocket-shaped structure configured to fit securely over the drainage end 104. Further, the drain cap 102 (hereforth also termed as cap 102) may prevent the accidental opening of the drain tab, a common concern among ostomy bag users. Furthermore, the cap 102 may ensure that the drainage end 104 remains securely closed, minimizing the risk of leaks and promoting user confidence. Moreover, the cap 102 may provide ease of application and removal as the user applies and removes the ostomy bag 100.

In an embodiment, the drain cap 102 may be soft and flexible, making it comfortable for the user. Further, the cap 102 may cushion the rigid or sharp edges of the drainage end, which can otherwise cause discomfort or irritation to the skin, especially during movement or when the bag is in use for extended periods. The cushioning may provide a more comfortable and user-friendly experience. Furthermore, the cap 102 may be made from stretchable materials that may facilitate the cap to securely stay in place on the drainage end, and prevent the drainage end from opening unintentionally. The stretchability of the material may ensure that the cap 102 adapts to various sizes and shapes of ostomy bag 100 drainage ends. The elasticity of the fabric may eliminate the need for additional fasteners, clips, or other attachment mechanisms, simplifying use and ensuring that the cap remains securely in position without requiring constant adjustment.

In an embodiment, the cap 102 may be reusable, withstanding multiple uses and cleaning cycles without significant loss of elasticity or structure. In an embodiment, the cap 102 may facilitate customization in size and shape to accommodate various ostomy bag designs. In one embodiment, the dimensions of the cap 102 may be adjusted to fit drainage ends of different sizes. The elasticity of the material may enable the cap 102 to adapt to these variations while maintaining its functionality. Additionally, the cap may be manufactured using alternative methods such as gluing, heat sealing, or extrusion, depending on the selected materials and desired production efficiency.

In an embodiment, the cap 102 may be available in various colors, allowing users to match it to their clothing or minimize its visibility under sheer fabrics. Further, the cap 102 may be adapted for other medical devices that require similar protective covers. For example, the cap 102 may be resized to fit other types of drainage bags or medical equipment with similar requirements. The construction and material composition of the cap may facilitate versatility and functionality across various applications.

In an embodiment, the cap 102 may be a rectangular pocket-shaped structure that slip easily onto the drainage end of the ostomy bag 100 when stretched. The elasticity of the material may facilitate the cap 102 to stay securely in place, while the thickness of the fabric may provide cushioning against the skin. In an embodiment, the cap 102 may be constructed and or assembled from a fabric material with two layers of polyester-spandex and with a neoprene layer sandwiched in-between, which provides additional comfort and protection.

In an embodiment, the fabric used may be composed of approximately 90% polyester and approximately 10% spandex, with a thickness of approximately 1.5 mm. A neoprene layer in the center may provide additional cushioning, helping prevent irritation caused by the sharp edges of the drainage end. Materials with less or no spandex do not provide sufficient stretch or retention of shape, which would prevent the cap from staying securely in place. In an embodiment, use of high-quality materials may ensure both comfort and functionality, addressing potential issues found with thinner, less elastic fabrics that do not adequately protect the skin.

Figure 2:
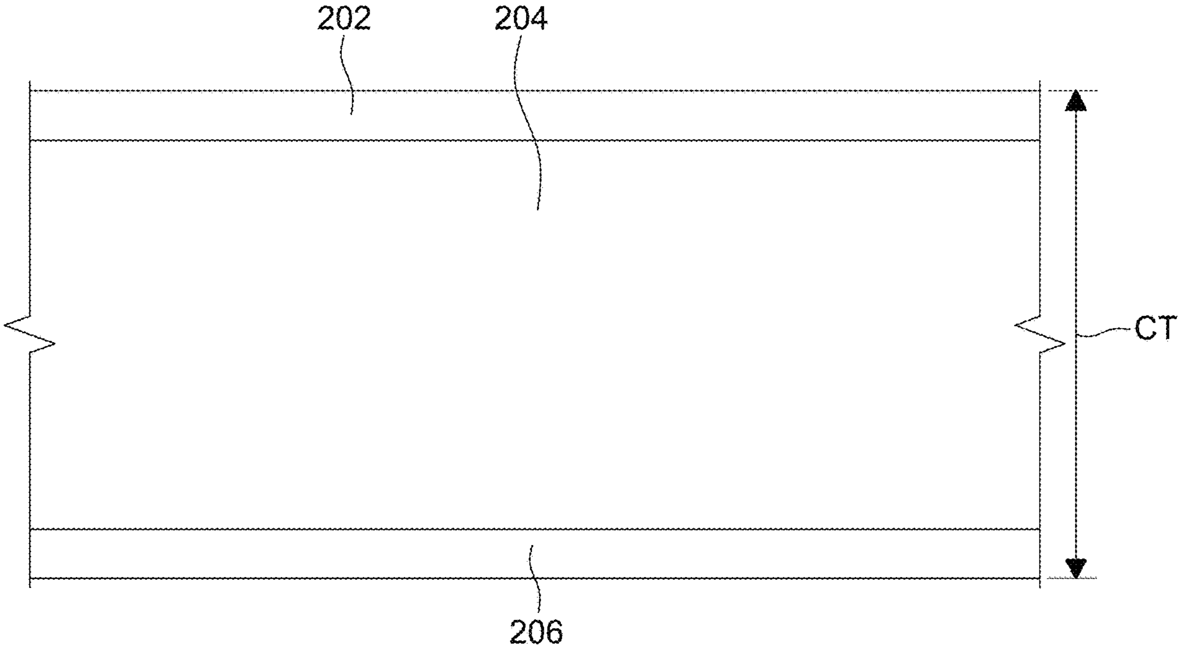
FIG. 2 is a side view of the edge of the material used to construct the drain cap and showing different layers, according to an illustrative embodiment.

FIG. 2 is a side view of the edge of the material used to construct the drain cap and showing different layers, according to an illustrative embodiment. In various embodiments, an outer layer 202 can be a stretchable, or elastic type of outer material. This outer stretchable material can be a fabric chosen for its ability to stretch in multiple directions. This can be referred to as a 4-way stretch fabric, as is known to one of skill in the art. In various embodiments, the outer 4-way stretchable material 202 can be a polyester spandex material, or other elastic materials that can be stretched and repeatedly return to their original size and shape. It should be clear that various possible elastic and/or stretchable materials are possible. The outer layer 202 can be a soft fabric that can be pleasing to the touch and comfortable to the user.

A padding layer 204 can be a middle layer in the fabric combination. Padding layer 204 can be a resilient, compressible material that can provide padding, such as neoprene or other resilient materials. The padding layer 204 can provide padding to prevent the edges of the drain end from rubbing on the skin of the user. The padding layer 204 can also provide a bulk or body to the cap, allowing it to remain in place and hold the drain end securely closed. It should be clear that various possible resilient, compressible materials are possible, however, resilient compressible fabrics such as neoprene may offer the best long-term durability. The resilient, compressible fabric used for the middle padding layer, such as neoprene, can be selected not just for the properties of proving padding and body, but also for the ability to withstand repeated stretching and repeated washings. It should be clear that various possible materials are possible.

In various embodiments, the cap may include an inner layer 206 that can be a stretchable, or elastic type of inner material. Inner layer 206 can be the same material as outer layer 202, or can be a different material. The inner stretchable material can be chosen for its ability to stretch in multiple directions, and can be a 4-way stretch fabric. In various embodiments, the inner 4-way stretchable material 206 can be a polyester spandex material, or other elastic materials that can be stretched and repeatedly return to their original size and shape. The inner stretch material can be in direct contact with the closed drain end, and by wrapping around the closed drain end, this stretchable material can help to hold the drain end closed. It should be clear that various possible elastic and/or stretchable materials are possible. The combination of stretchable elastic outer fabrics, combined with the resilient or compressible inner material can work together to hold the cap in place, prevent opening of the drain end, and protect the skin of the user.

In various embodiments, the layers of material may have a combined thickness CT of between approximately 2 mm and approximately 1 mm. In various embodiments, the layers of material may have a combined thickness CT of approximately 1.5 mm. In various embodiments, the layers of material may have a combined thickness CT of approximately 3 mm or thicker. The fabric used for the construction may stretch in both lengthwise and widthwise directions, unlike some materials that only stretch in one direction or do not stretch at all. This 4-way stretch may ensure that the cap 102 stays in place and offers protection from the drainage end of the bag accidentally opening, especially if it has not been fully closed. The combination of stretchable elastic fabrics, such as polyester-spandex, combined with the inner layer of compressible resilient material such as neoprene, work together to compress around the drainage end and prevent unintentional opening, while also providing a resilient padding that can cover the edges of the drain opening and prevent the drain opening from rubbing the skin of the user. The combination of materials used can provide a soft, pleasant exterior that can be comfortable to the touch, and a padded body that can protect the user from pointy edges.

In an embodiment, the cap 102 may be assembled by cutting the fabric, folding it, and securing the ends with a straight stitch using polyester-wrapped core-spun thread, which ensures durability under repeated use and washing. In an embodiment, the end seams may be zigzag stitched, although a straight stitch with ⅛" seam allowances may be sufficient to maintain a trim and non-bulky structure. The cap 102 may then be turned inside out to conceal the seams, thereby providing a clean finish.

Figure 3A:
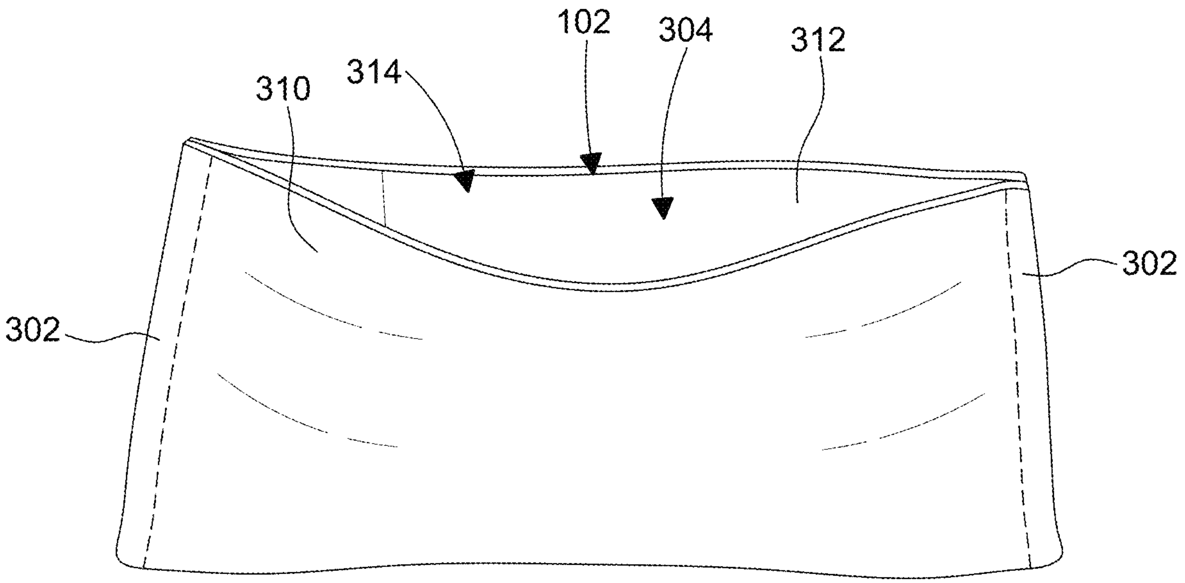
FIG. 3A is a front view of a relaxed drain cap with seams at the sides, and shown inside out, according to an illustrative embodiment.

FIG. 3A illustrates a front view of a relaxed drain cap 102 with seams 302 at the sides, and shown inside out, in accordance with an embodiment of the present disclosure. In various embodiments, a method of constructing a drain cap 102 can include starting with a multi-layered starting material or materials, such as two layers of polyester-spandex with a layer of neoprene sandwiched between the layers of polyester-spandex. In various embodiments, the drain cap can be a pocket that is defined by a front panel 310, a back panel 312, and an opening 314. In various embodiments, the pocket can be formed from a single, unitary piece of fabric that can be folded to form a front panel and a back panel. In various embodiments, the unitary piece of fabric can be two layers or three layers of material sandwiched together.

In an embodiment, the multi-layered starting material may be an approximately 3" long by approximately 2½" wide piece, which may be folded in half to form a pocket with dimensions of approximately 3" by 1¼". However, it should be clear that various sizes and various dimensions are possible. As shown, the multi-layered starting material can be folded over and the edges can be sewn, glued, or otherwise fixed together to form an inside-out pocket 304 with seams 302. After the sides are fixed together, the pocket can be inverted so that the sewn seams 302 are inside of the pocket 304. The seams can be located along the sides and/or bottom of the pocket, so that they are located next to the sides of the folded or rolled drainage end. That is to say, when the drainage end is folded up flat, the seams may surround and/or abut the sides of the folded up drainage end. In this way, the seams and the rigid sides of the drainage end are in alignment and can work together to keep the drain cap in place over the drainage end, even when the drain cap is exposed to forces such as repeated brushes with clothing while walking.

Figure 3B:
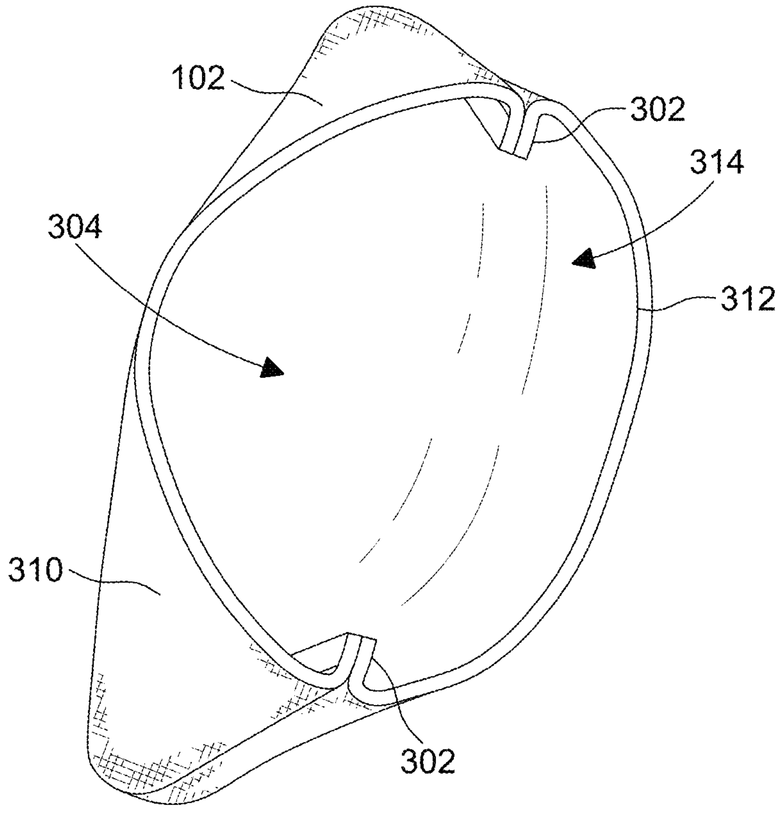
FIG. 3B is a perspective view of a relaxed drain cap of FIG. 3A with side seams on the inside, according to an illustrative embodiment.
Figure 3C:
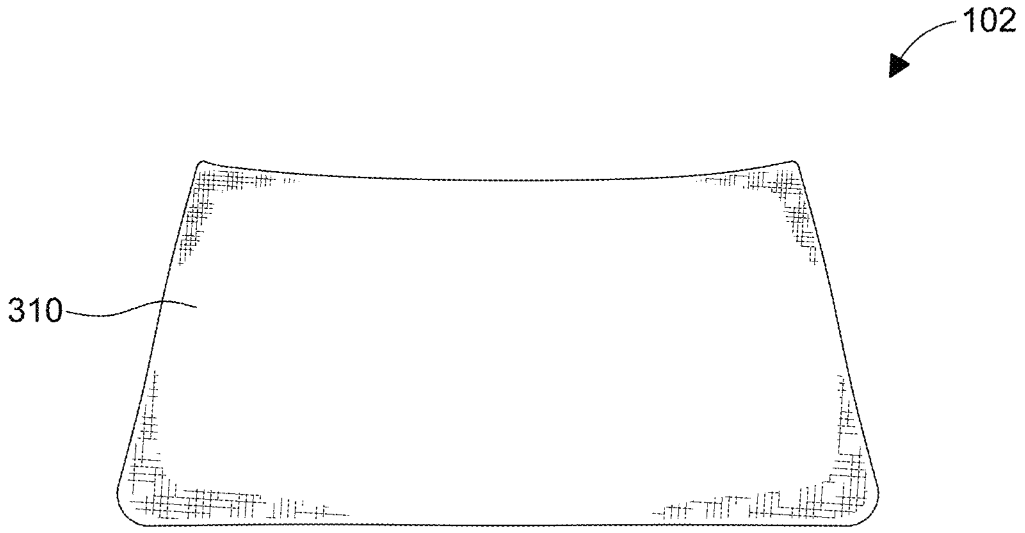
FIG. 3C is a front view of the relaxed drain cap of FIG. 3B, according to an illustrative embodiment.
Figure 3D:
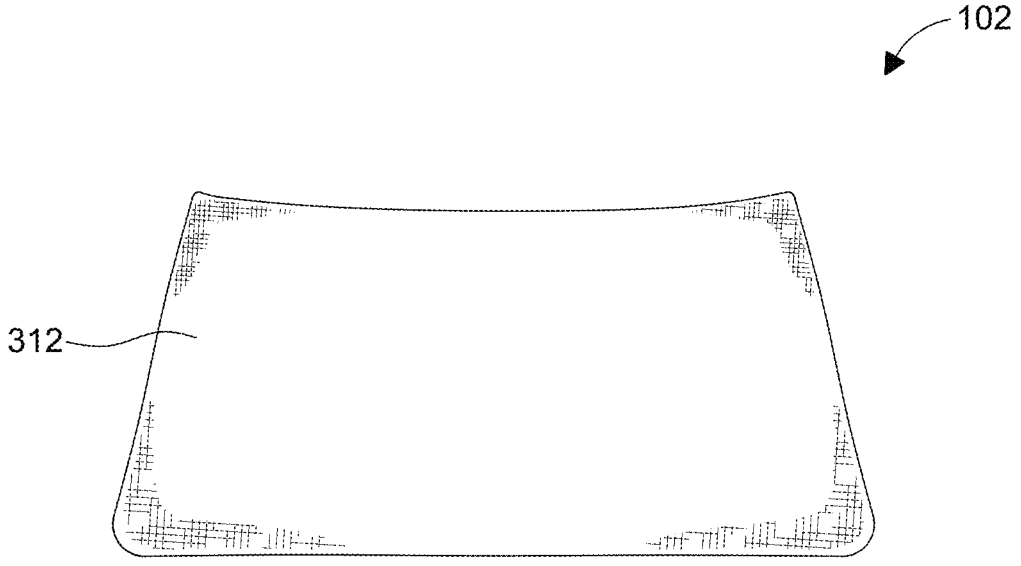
FIG. 3D is a rear view of the relaxed drain cap of FIG. 3B, according to an illustrative embodiment.
Figure 3E:
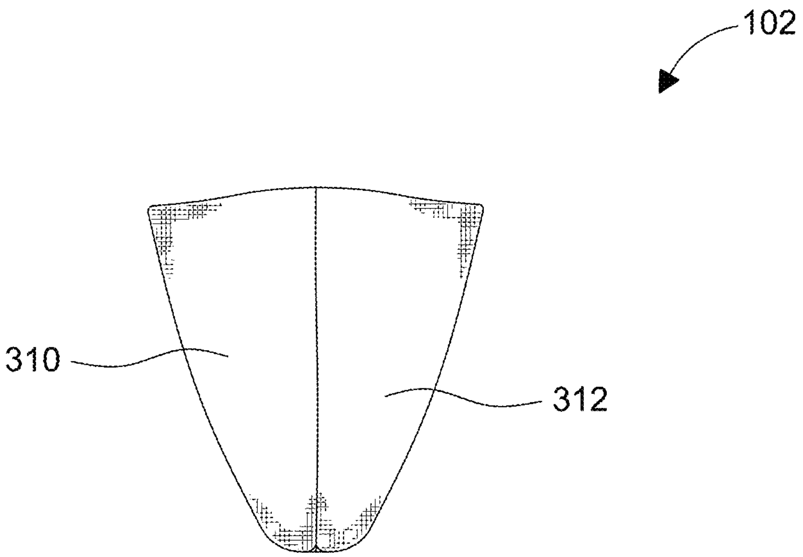
FIG. 3E is a right side view of the relaxed drain cap of FIG. 3B, according to an illustrative embodiment.
Figure 3F:
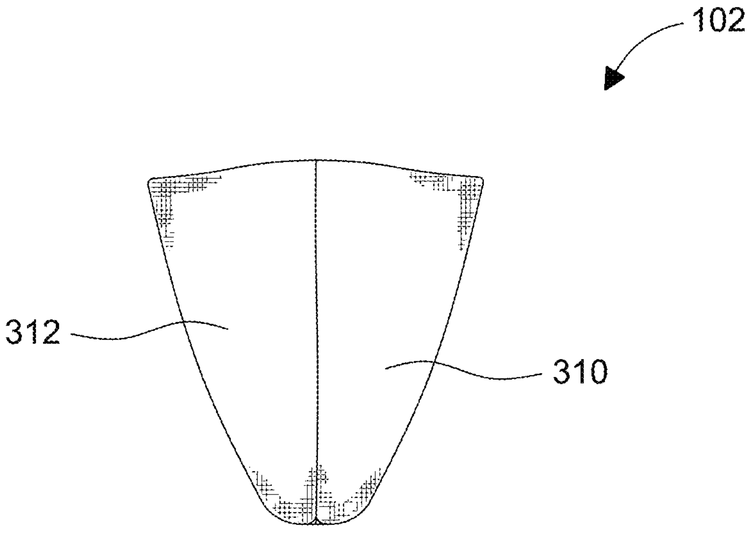
FIG. 3F is a left side view of the relaxed drain cap of FIG. 3B, according to an illustrative embodiment.
Figure 3G:
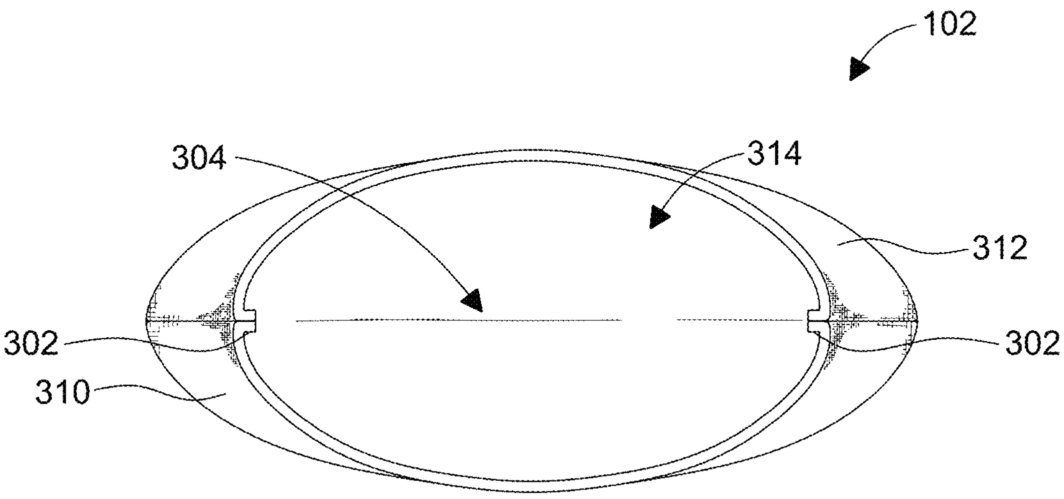
FIG. 3G is a top view of the relaxed drain cap of FIG. 3B, according to an illustrative embodiment.
Figure 3H:
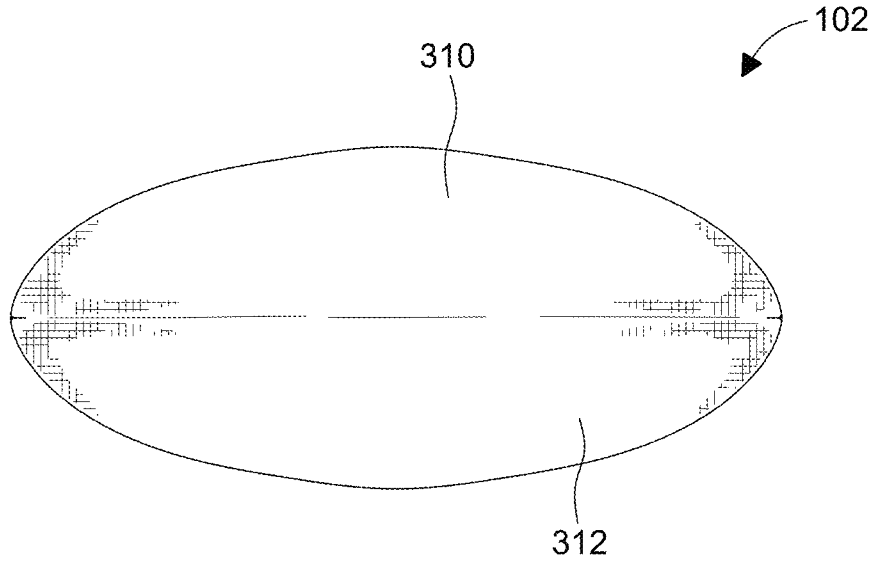
FIG. 3H is a bottom view of the relaxed drain cap of FIG. 3B, according to an illustrative embodiment.

The sides may be sewn with ⅛" seam allowances to hold the shape. The top edge of the pocket may be left straight or cut using pinking shears for a decorative finish. The pocket can then be turned inside out to form the completed cap. FIG. 3B illustrates a perspective view of a relaxed drain cap of FIG. 3A with side seams on the inside, and ready for use, according to an illustrative embodiment. FIG. 3C is a front view of the relaxed drain cap of FIG. 3B, according to an illustrative embodiment. FIG. 3D is a rear view of the relaxed drain cap of FIG. 3B, according to an illustrative embodiment. FIG. 3E is a right side view of the relaxed drain cap of FIG. 3B, according to an illustrative embodiment. FIG. 3F is a left side view of the relaxed drain cap of FIG. 3B, according to an illustrative embodiment. FIG. 3G is a top view of the relaxed drain cap of FIG. 3B, according to an illustrative embodiment. FIG. 3H is a bottom view of the relaxed drain cap of FIG. 3B, according to an illustrative embodiment.

FIGS. 3B-3H are described together. The front panel 310 and the back panel 312 can define a pocket 304 with an opening 314. The cap is now ready to be stretched and wrapped around the closed drain end so that it can secure and protect the drainage and of an ostomy bag.

In an embodiment, the drain cap 102 may be reusable and washable. Hand washing may preserve the integrity of the materials, but machine washing followed by air drying may also be possible. The cap can be assembled or sewn together with threads that can be selected for their ability to withstand repeated washings, dryings, and reusages. The use of polyester-wrapped core-spun thread may ensure that the seams hold up well to repeated stretching and usage, unlike cheaper cotton threads that may break or degrade over time.

Figure 3I:
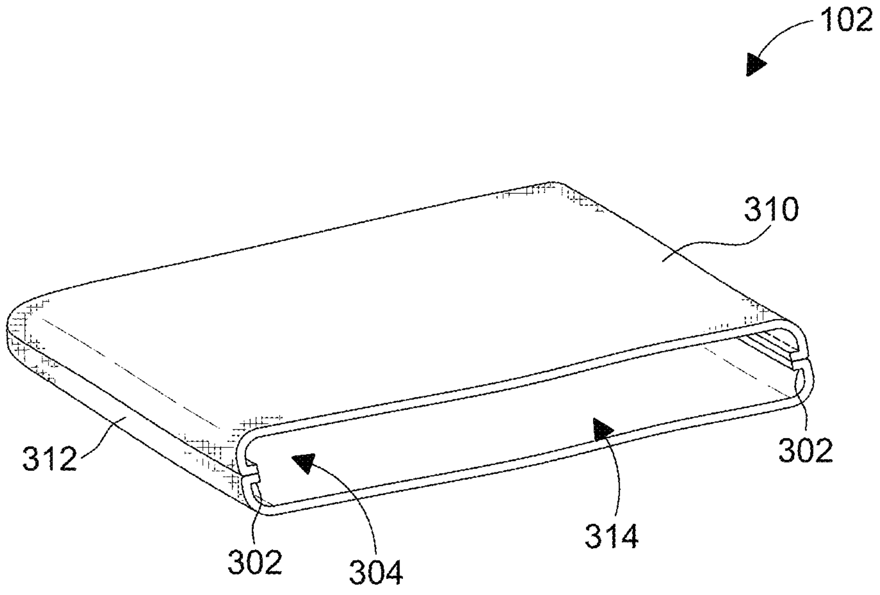
FIG. 3I is a perspective view of the drain cap of FIG. 3B, shown as applied to an ostomy drain, according to an illustrative embodiment.
Figure 3J:
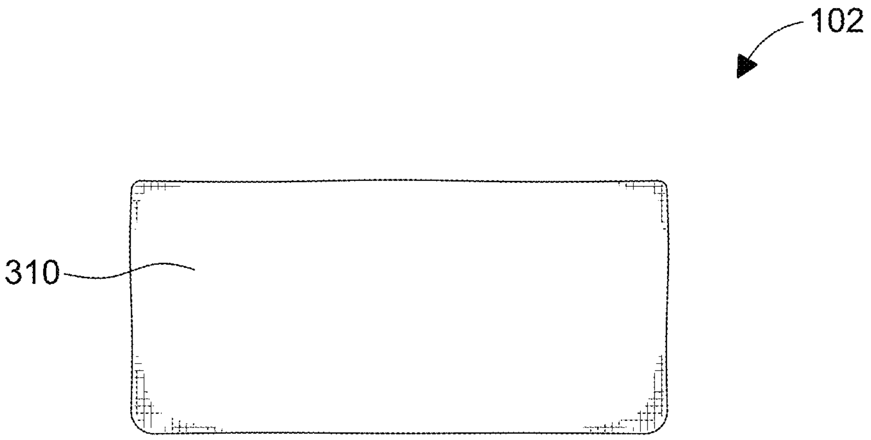
FIG. 3J is a front view of the drain cap of FIG. 3I, according to an illustrative embodiment.
Figure 3K:
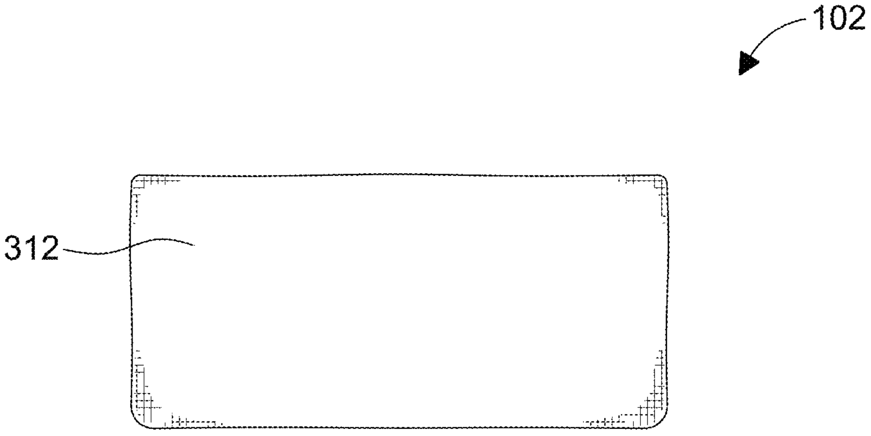
FIG. 3K is a rear view of the drain cap of FIG. 3I, according to an illustrative embodiment.
Figure 3L:
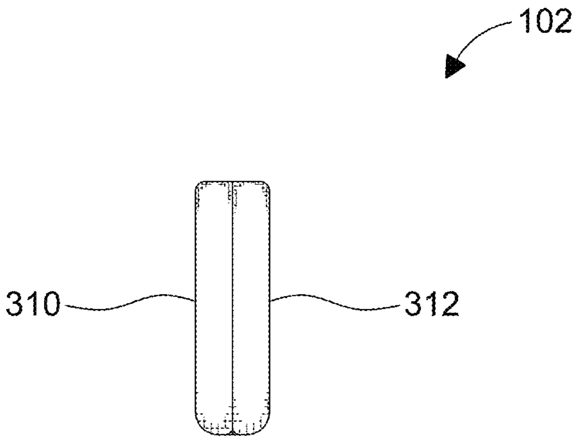
FIG. 3L is a right side view of the drain cap of FIG. 3I, according to an illustrative embodiment.
Figure 3M:
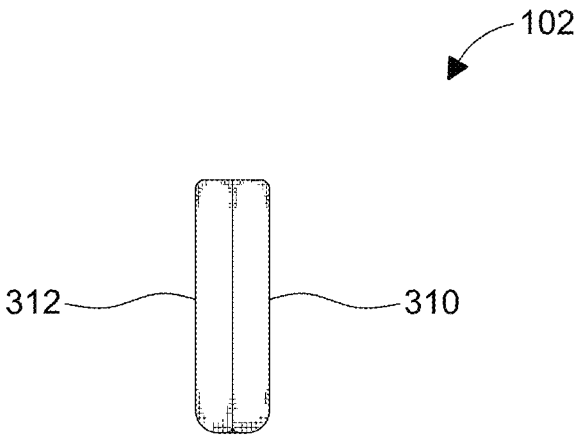
FIG. 3M is a left side view of the drain cap of FIG. 3I, according to an illustrative embodiment.
Figure 3N:
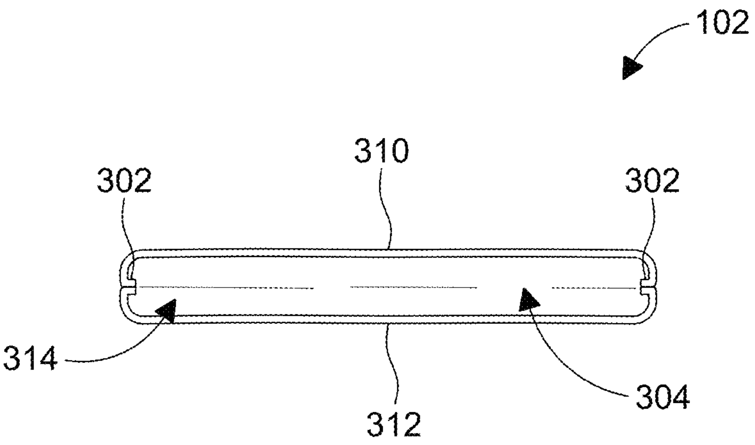
FIG. 3N is a top view of the drain cap of FIG. 3I, according to an illustrative embodiment.
Figure 3O:
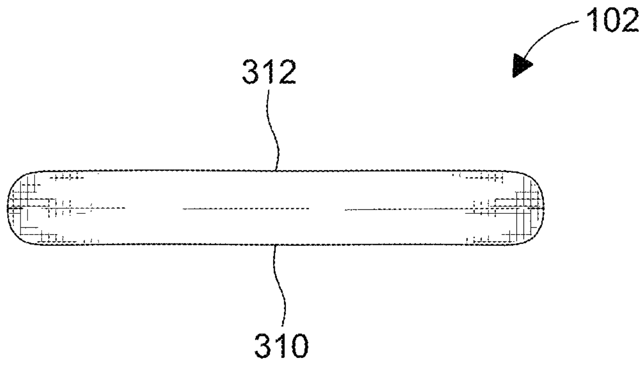
FIG. 3O is a bottom view of the drain cap of FIG. 3I, according to an illustrative embodiment.

FIG. 3I is a perspective view of the drain cap of FIG. 3B, shown as applied to an ostomy drain, according to an illustrative embodiment. FIG. 3J is a front view of the drain cap of FIG. 3I, according to an illustrative embodiment. FIG. 3K is a rear view of the drain cap of FIG. 3I, according to an illustrative embodiment. FIG. 3L is a right side view of the drain cap of FIG. 3I, according to an illustrative embodiment. FIG. 3M is a left side view of the drain cap of FIG. 3I, according to an illustrative embodiment. FIG. 3N is a top view of the drain cap of FIG. 3I, according to an illustrative embodiment. FIG. 3O is a bottom view of the drain cap of FIG. 3I, according to an illustrative embodiment. FIGS. 3I-3O are described together. As shown in FIGS. 3I-3O, the drain cap is shown in a shape an conformation it can have when it has been applied to the drain end. When the drain cap is applied to the drain of the ostomy bag, it is stretched around the drain end so that the drain cap holds the drain end closed. The front side 310 and rear side 312 can be pressed against the front and back of the closed drain end, and the drain cap can secure the drain end in position and prevent the drain end from unrolling or otherwise opening. By wrapping tightly around the closed drain end, the drain cap 102 prevents the drain end from opening.

Figure 4A:
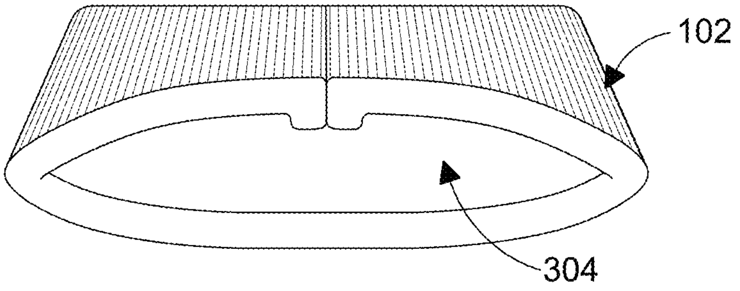
FIG. 4A is a top view of a stretched drain cap, according to an illustrative embodiment.
Figure 4B:
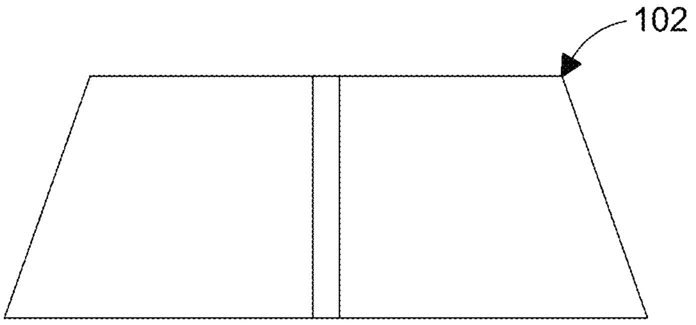
FIG. 4B is a front view of a stretched drain cap, according to an illustrative embodiment.
Figure 5A:
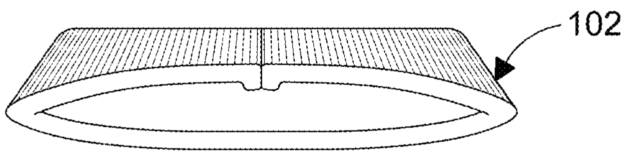
FIG. 5A is a top view of a relaxed drain cap, according to an illustrative embodiment.
Figure 5B:
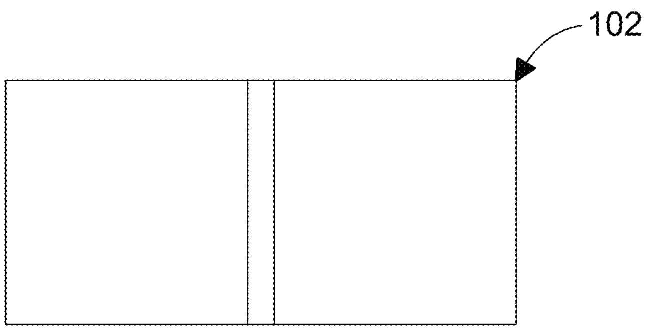
FIG. 5B is a front view of a relaxed drain cap, according to an illustrative embodiment.

FIG. 4A illustrates a top view of stretched drain cap 102, in accordance with an embodiment of the present disclosure. FIG. 4B illustrates a front view of the stretched drain cap 102, in accordance with an embodiment of the present disclosure. FIG. 5A illustrates a top view of a relaxed drain cap 102, in accordance with an embodiment of the present disclosure. FIG. 5B illustrates a front view of the relaxed drain cap 102, in accordance with an embodiment of the present disclosure. In various embodiments, a method of constructing a drain cap 102 can include starting with a multi-layered starting material or materials, such as two layers of polyester-spandex with a layer of neoprene sandwiched between the layers of polyester-spandex. In an embodiment, the multi-layered starting material may be an approximately 6" long by approximately 1¼" wide piece, which may be folded over to form a pocket with dimensions or approximately 3" by 1¼". However, it should be clear that various sizes and various dimensions are possible. In various embodiments, the multi-layered starting material can be folded over and the ends of the fabric strip can be fixed together for form a ring, and then the bottom edge can be fixed together to form a pocket. The vertical seam and the bottom edge can be sewn, glued, or otherwise fixed together to form an inside-out pocket. After the seams are fixed together, the pocket can be inverted so that the seams are inside of the pocket. The seams may be sewn with ⅛" seam allowances to hold the shape. The top edge of the pocket may be left straight or cut using pinking shears for a decorative finish.

The drain cap 102 can be stretched out, for example, by inserting fingers into the pocket 304 and pulling outwards on the sides of the cap to increase the size of the opening of the pocket. The stretched cap 102 can then be placed around the folded up drainage end and allowed to relax, allowing the cap to return to the relaxed and unstretched shape in position around the folded drainage end. The cap can then hold the drainage end in the folded shape and prevent unrolling.

Figure 6A:
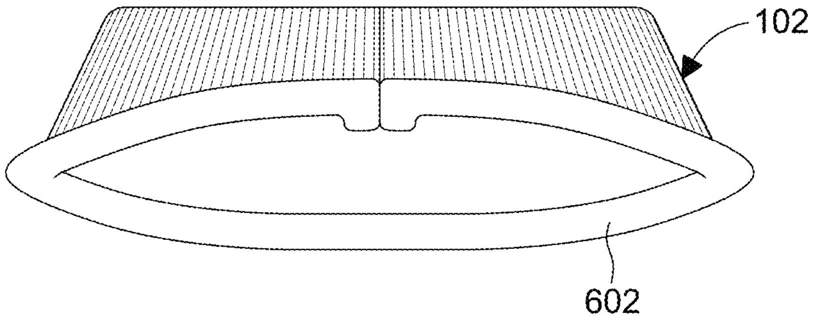
FIG. 6A is a top view of a stretched drain cap with a reinforced, elasticized trim, according to an illustrative embodiment.
Figure 6B:
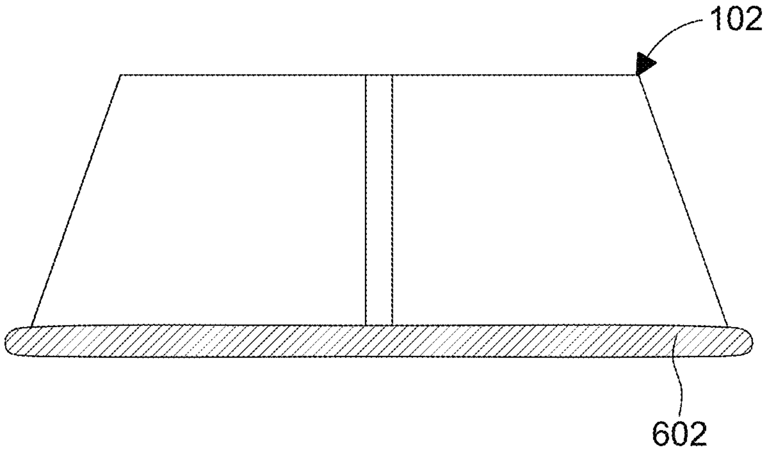
FIG. 6B is a front view of a stretched drain cap with a reinforced, elasticized trim, according to an illustrative embodiment.

FIG. 6A illustrates a top view of a stretched drain cap with a reinforced, elasticized retention band, in accordance with an embodiment of the present disclosure, and FIG. 6B illustrates a front view of a stretched drain cap with a reinforced, elasticized retention band, in accordance with an embodiment of the present disclosure. A drain cap 102 can have an elastic retention band 602 that can also be referred to as an elasticized trim. The elasticized retention band 602 can help to ensure that the cap does not accidentally become disengaged from the drain end. The elastic retention band 602 can be stretched around the folded drain end, and the elastic trim 602 can be allowed to contract with the folded drain end within the pocket. In this way, the elastic retention band can further prevent the folded drain end from slipping out of the pocket. This elasticized trim 602 may provide an additional layer of elasticity at the top, making the cap 102 more secure and ensure that the cap 102 fits snugly around the drainage end 104. The reinforced trim may be made from a stretchable fabric or an elastic band sewn into the edge of the cap 102. Such drain cap may offer extra durability and a more secure fit for users who experience more movement or for those who wear their ostomy bags in more active settings. The reinforced edge may also help prevent the cap from slipping off if the drainage tab is not securely closed.

The drain cap 102 may be a rectangular pocket shaped structure configured to fit over drainage end 104 of an ostomy bag 100. The pocket may be formed from fabrics that can include two layers of polyester-spandex and a layer of neoprene sandwiched between the two layers of polyester-spandex. The layered construction (manufactured or assembled) may allow the fabric to offer both elasticity and cushioning, ensuring a secure fit over the drainage end and protection against skin irritation caused by sharp or rigid edges. Further, the pocket may be formed by cutting the fabric into a rectangular piece, folding the piece in half, and securing the sides with ⅛" seam allowances which may ensure a smooth, non-bulky finish that contributes to the comfort and durability of the cap 102.

In an embodiment, the pocket may be configured to fit over the drainage end 104 of the ostomy bag 100 by way of sliding in a stretched form, such that the pocket stays in place in an original form. Further, the pocket may be removed from the drainage end 104 of the ostomy bag 100 by way of stretching and sliding back. The elasticity of the polyester-spandex fabric may ensure that the pocket maintains its original form, providing a snug and stable fit over the drainage end without slipping off. To remove the drain cap 102, user may stretch the pocket and slide it back off the drainage end 104 with minimal effort. The easy-to-use design may facilitate quick application and removal, making the drain cap 102 practical for regular use.

In an embodiment, the pocket may be manufactured using methods such as, sewing, gluing, heat pressing, and/or extruding. Also, the pocket may be configured to be reusable and washable. In an embodiment, the top edge of the pocket may be straight and/or cut. The manufacturing methods may facilitate for the creation of a durable and well-constructed pocket that is both functional and comfortable. Additionally, the drain cap 102 may be designed to be reusable and washable, offering the benefit of longevity and ease of maintenance for the user. In an embodiment, the top edge of the pocket may be left straight, or alternatively, it may be cut using pinking shears or another decorative cutting method for aesthetic purposes. This feature gives the drain cap 102 versatility in both function and appearance, making it adaptable to different user preferences.

In an embodiment, the fabric provides sufficient elasticity to secure the pocket in place during use. The elasticity may allow the pocket to fit snugly over the drainage end 104 of the ostomy bag 100, preventing the cap 102 from shifting or coming loose. Further, the fabric may have a thickness to provide cushioning against the drainage end of the ostomy bag preventing skin irritation caused by contact with sharp and rigid edges. Further, the fabric may have approximately 90% polyester and approximately 10% spandex. The fabric may have a thickness that can be approximately 1.5 mm. Furthermore, fabric may stretchable in both lengthwise and widthwise directions to ensure secure attachment to the drainage end of the ostomy bag 100. The two-way stretch may ensure that the drain cap 102 stays in place, even if the shape or size of the drainage end 104 changes slightly. The stretchability of the fabric may ensure a secure attachment to the drainage end 104 of the ostomy bag 102, preventing accidental dislodging or discomfort.

In an embodiment, seams of the drain cap can be sewn using polyester wrapped core-spun thread. The polyester wrapped core-spun thread may ensure that the seams remain intact under regular use and washing, contributing to the longevity of the drain cap.

In an embodiment, the fabric may tightly wrap around the drainage end 104 of the ostomy bag 100 end, conforming to its contours. The elasticity of the polyester-spandex material may enable the cap 102 to remain securely in place during use, preventing it from sliding off or moving around, even when the ostomy bag 100 is in motion. The neoprene layer in the center of the fabric may provide soft cushioning that shields the user's skin from discomfort caused by the edges of the ostomy bag's drainage tab. The protective cushioning may also help prevent any accidental opening of the drainage end, ensuring that the cap stays in place and offers both security and comfort to the user. Seams at both ends of the cap 102 may be secured with ⅛" seam allowances using polyester-wrapped core-spun thread to ensure durability and a tight finish. The seams of the cap may be neatly folded inside the cap, ensuring a smooth, non-abrasive surface for the user. The lack of visible seams on the exterior contributes to the comfort and discretion of the device when worn.

In an embodiment, the fabric of the cap 102 may return to its original, compact shape after being removed from the drainage end 104 of the ostomy bag 102. Further, the fabric may retain enough elasticity to be reused multiple times without losing its shape or effectiveness. Furthermore, despite being in a relaxed state, the cap 102 may can be stretched back over the ostomy bag's drainage end when needed. Even in relaxed state, the fabric may maintain its shape without becoming overly rigid or stiff after multiple uses. In various embodiments, the layers of material may have a combined thickness of between approximately 2 mm and approximately 1 mm. In various embodiments, the layers of material may have a combined thickness of approximately 1.5 mm. The material's thickness which may be approximately 1.5 mm, along with the combination of polyester-spandex and neoprene, may ensure that the cap remains durable, even when in its relaxed state, and ready to provide comfort and protection when stretched. The cap 102 may maintain its functionality over time and provide consistent protection and comfort, regardless of whether it is in a stretched or relaxed state. Additionally, the fabric in the relaxed state ensures the cap's reusability, with the option to hand wash and air dry to maintain its durability.

In an embodiment, the cap may be small and compact which may allow it to be conveniently stored or easily handled. Further, the cap may be fold or bend, making it easy to store or prepare for future use. The neoprene layer within the fabric may provide cushioning properties, even when the cap is not in use.

In various embodiments, the drain cap 102 may have variations in its construction, materials, and design features, providing flexibility for different user preferences and functional requirements. The fabric used for the drain cap 102 may be made entirely from a different blend of stretchable materials, such as elastane or Lycra, combined with a thinner layer of foam for cushioning. The foam layer may be provide a more lightweight option while still offering some cushioning to protect the user's skin. The lightweight drain cap may be suitable for users who may prefer a less bulky cap but still require a degree of comfort and skin protection from the drainage end of the ostomy bag. The reduced thickness of the foam may make the cap easier to fit in tighter spaces or for those who have ostomy bags with smaller drainage ends.

In an another embodiment, the cap 102 may be made with antimicrobial or hypoallergenic materials for users with sensitive skin. The fabric may be treated with antimicrobial agents to prevent bacterial growth and reduce the risk of skin irritation or infections, a common concern for ostomy bag users. The hypoallergenic fabric may provide additional comfort for those with sensitive skin or allergies to certain materials. Such caps may be particularly useful for individuals who wear the ostomy bag for extended periods and are looking for added protection against skin irritation and discomfort.

In yet another embodiment, the drain cap 102 may feature an integrated, removable liner or insert. The liner may be made from a soft, moisture-wicking fabric that may help keep the skin dry and comfortable. The insert may be easily removable for cleaning or replacement and could be made from a fabric such as cotton or bamboo. The liner may be especially beneficial for users who experience increased moisture around the drainage end and would like an extra layer to absorb excess moisture while still maintaining the cushioning and protective benefits of the main cap.

Figure 7:
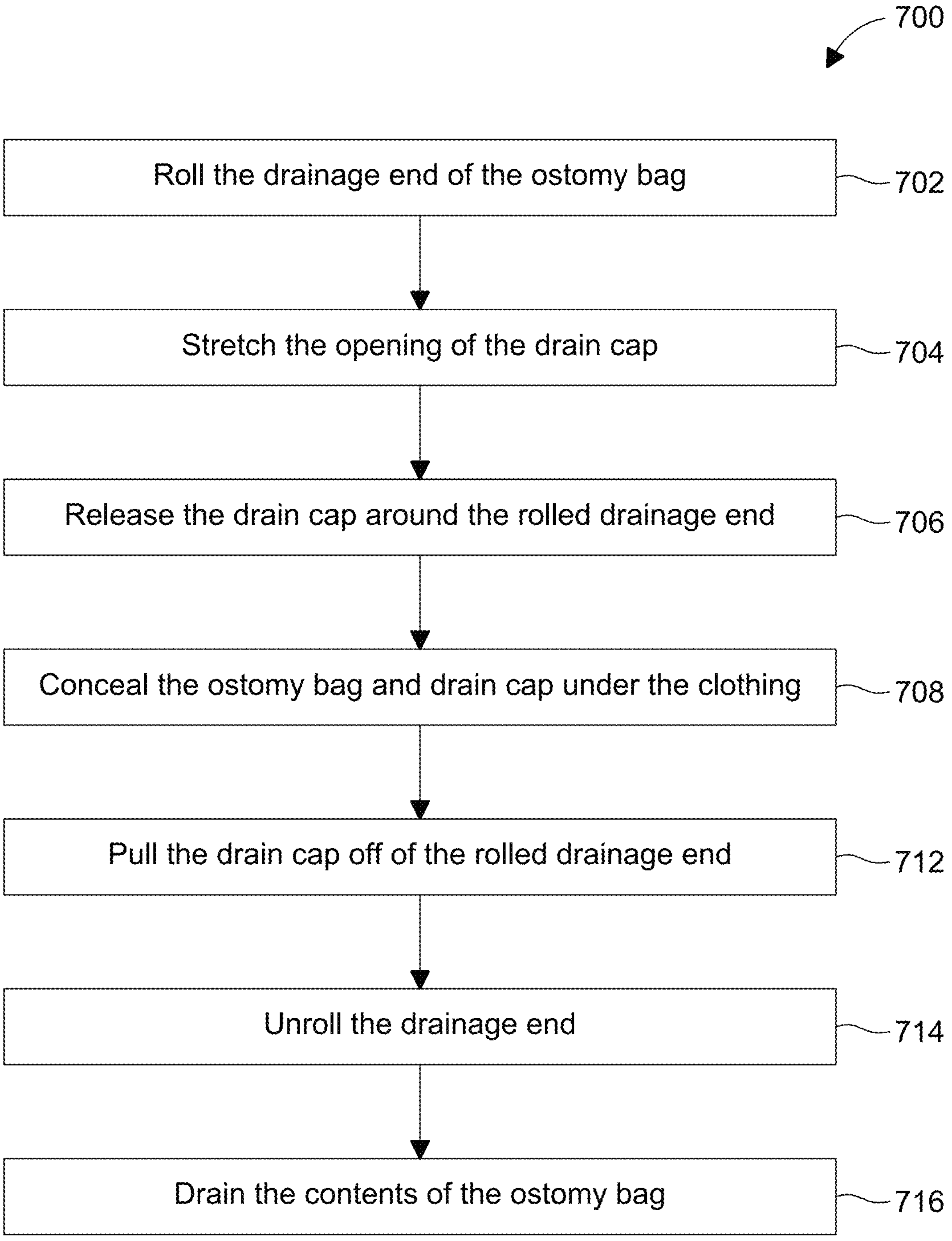
FIG. 7 is a chart showing a method of using an ostomy bag drain cap, according to an illustrative embodiment.

FIG. 7 illustrates a method 700 of using an ostomy bag drain cap, in accordance with an embodiment of the present disclosure. At box 702, a user can roll or fold the drainage end of an ostomy bag into a rolled conformation. At box 704, the user can stretch the opening of an ostomy bag drain cap, and can place the ostomy bag drain cap around the rolled drainage end. At box 706, the user can release the cap around the rolled drainage end. The stretchable outer layer and/or inner layer of the drain cap can contract around the rolled drainage end. As the stretchable layer(s) contract around the rolled drainage end, they can secure the rolled drainage end in the rolled and closed shape. Releasing the cap around the rolled drainage end allows the cap to prevent the rolled drainage end from accidentally unrolling and opening. Releasing the cap around the rolled drainage end can lock the drainage end in the rolled and folded position. At box 708, the user can conceal the ostomy bag and drain cap under the user's clothing. The drain cap can prevent the clothing of the user from catching on the folded drainage end and accidentally opening the drainage end. The drain cap can keep the folded drainage end folded, even when the end is tugged on by the user's clothing. The folded drainage end and the drain cap can create a two-part system that can work together to create a safe, secure, soft, and comfortable closure that keeps the user's clothes clean with the contents of the ostomy bag held safely inside, while also protecting the skin of the user under the user's clothing from unwanted contact with the hard plastic corners of the rolled drainage end.

At box 712, the user can pull the cap off of the rolled and folded drainage end. Removing the cap from the rolled and folded drainage end can unlock the drainage end so that it can be unrolled. At box 714, the user can unroll the drainage end, thereby opening the drainage of the ostomy bag. At box 716, the user can drain the contents of the ostomy bag. The user can then re-roll the drainage end and replace the cap, thereby returning the drainage end to the closed and locked conformation.

The described ostomy bag drain cap (hereforth termed as described apparatus) provides a transformative solution to several challenges faced by ostomy bag users. The described apparatus addresses key problems associated with traditional ostomy bag drainage systems, offering significant advantages in both functionality and user comfort. Traditional drainage systems often expose users to risks of accidental openings, skin irritation from rigid edges, and discomfort from direct contact with sharp corners. These issues compromise the quality of life and discretion for individuals relying on ostomy bags. The described apparatus eliminates such drawbacks by providing a stretchy, snug-fitting, and cushioned cover for the drainage end. Further, the described apparatus securely covers the drainage end of the ostomy bag, preventing accidental openings that can lead to leaks and discomfort. This layer of protection provided by the described apparatus significantly improves the overall reliability of ostomy systems.

The described apparatus also prevents skin irritation caused by contact with the rigid and sharp edges of the drainage end. The inclusion of a neoprene core sandwiched between polyester-spandex layers may create a cushioned barrier that protects the skin, offering relief to users who experience discomfort or sensitivity. This cushioned barrier enhances the described apparatus suitability for extended wear, ensuring both comfort and functionality throughout the day.

Moreover, the combination of bi-directionally stretchable polyester-spandex with neoprene not only allows the cap to adapt to various drainage end sizes and shapes but also ensures it remains securely in place without additional fasteners. This elasticity simplifies application and removal, making the described apparatus accessible for individuals with varying levels of dexterity. Unlike non-elastic or rigid materials, the described apparatus conforms naturally to the drainage end, reducing the likelihood of slippage or misalignment.

Additionally, durability and reusability further set the described invention apart. The cap is designed to withstand repeated use without compromising its structural integrity, making it a cost-effective and environmentally friendly alternative to disposable covers. The materials used, including polyester-wrapped core-spun thread, ensure that the seams remain intact even after frequent stretching and washing. Users can hand-wash and air-dry the cap without risking degradation, preserving its performance over an extended period. This durability not only reduces waste but also lowers long-term costs for users.

Finally, as the design of the described apparatus is highly versatile, its uses may extend beyond ostomy bags to other medical devices with similar drainage ends. The described apparatus adaptability in terms of size and shape accommodates a broad spectrum of user needs, ensuring a customized fit for different systems. Additionally, the availability of multiple color options enhances discretion, especially for users concerned about visibility under clothing. These advantages collectively position the disclosed apparatus as a superior solution in ostomy care, addressing both functional and aesthetic requirements while prioritizing user comfort and convenience.

Overall, the described apparatus addresses key problems associated with traditional ostomy bag drainage systems, offering significant advantages in both functionality and user comfort.

While embodiments of the present disclosure have been illustrated and described, it will be clear that the disclosure is not limited to these embodiments only. Numerous modifications, changes, variations, substitutions, and equivalents will be apparent to those skilled in the art, without departing from the spirit and scope of the disclosure, as described in the claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

While the foregoing describes various embodiments of the described apparatus, other and further embodiments of the described apparatus may be devised without departing from the basic scope thereof. The scope of the description is determined by the claims that follow. The description is not limited to the described embodiments, versions, or examples, which are included to enable a person having ordinary skill in the art to make and use the described apparatus when combined with information and knowledge available to the person having ordinary skill in the art.

While embodiments of the present disclosure have been illustrated and described, it will be clear that the disclosure is not limited to these embodiments only. Numerous modifications, changes, variations, substitutions, and equivalents will be apparent to those skilled in the art, without departing from the spirit and scope of the disclosure, as described in the claims.

While the foregoing describes various embodiments of the disclosure, other and further embodiments of the disclosure may be devised without departing from the basic scope thereof. The scope of the disclosure is determined by the claims that follow. The disclosure is not limited to the described embodiments, versions, or examples, which are included to enable a person having ordinary skill in the art to make and use the disclosure when combined with information and knowledge available to the person having ordinary skill in the art.

The invention claimed is:

1. An ostomy bag drain cap comprising:
a pocket configured to fit over a rolled drainage end of an ostomy bag, the pocket comprising:
a front panel made from a layered fabric;
a back panel made from the layered fabric; and
an opening at a top of the pocket adapted to allow the rolled drainage end to be inserted into the pocket,
wherein the layered fabric comprises:
an outer layer of 4-way stretchable fabric adapted to provide elasticity and to secure the pocket around a rolled drainage end during use; and
a padding layer of compressible and resilient fabric inside of the outer layer of 4-way stretchable fabric, the padding layer providing body and providing cushioning around the drainage end to prevent skin irritation caused by contact with the rolled drainage end.

2. The ostomy bag drain cap of claim 1, wherein the layered fabric further comprises an inner layer of 4-way stretchable fabric adapted to provide elasticity and to secure the pocket around the rolled drainage end during use, wherein the padding layer is sandwiched between the inner layer and the outer layer.

3. The ostomy bag drain cap of claim 1, wherein the outer layer of 4-way stretchable fabric further comprises approximately 90% polyester and approximately 10% spandex.

4. The ostomy bag drain cap of claim 1, wherein the padding layer of compressible and resilient fabric further comprises a neoprene.

5. The ostomy bag drain cap of claim 1, wherein the layered fabric has a combined thickness in a range between approximately 1 mm and approximately 2 mm.

6. The ostomy bag drain cap of claim 1 further comprising an elasticized retention band encircling the opening of the pocket.

7. The ostomy bag drain cap of claim 1, further comprising side seams that connect the front panel and the back panel along the sides of the pocket so that the side seams are adapted to align with the sides of the rolled drainage end.

8. An ostomy sanitation system comprising:
an ostomy bag comprising:
a pouch for storage of waste materials; and
a drainage end with a chute configured to be closed by rolling the end of the end chute to create a rolled seal; and
a drain cap comprising:
a pocket configured to fit over the drainage end of an ostomy bag when the drainage end is rolled, the pocket comprising:
a front panel made from a layered fabric;
a back panel made from the layered fabric; and
an opening at a top of the pocket adapted to allow the rolled drainage end to be inserted into the pocket,
wherein the layered fabric comprises:
an outer layer of 4-way stretchable fabric adapted to provide elasticity and to secure the pocket around a rolled drainage end during use; and
a padding layer of compressible and resilient fabric inside of the outer layer of 4-way stretchable fabric, the padding layer providing body and providing cushioning around the drainage end to prevent skin irritation caused by contact with the rolled drainage end.

9. The ostomy bag drain cap of claim 8, wherein the layered fabric further comprises an inner layer of 4-way stretchable fabric adapted to provide elasticity and to secure the pocket around the rolled drainage end during use, wherein the padding layer is sandwiched between the inner layer and the outer layer.

10. The ostomy bag drain cap of claim 1, wherein the outer layer of 4-way stretchable fabric further comprises approximately 90% polyester and approximately 10% spandex.

11. The ostomy bag drain cap of claim 1, wherein the padding layer of compressible and resilient fabric further comprises a neoprene.

12. The ostomy bag drain cap of claim 1, wherein the layered fabric has a combined thickness in a range between approximately 1 mm and approximately 2 mm.

13. The ostomy bag drain cap of claim 1 further comprising an elasticized retention band encircling the opening of the pocket.

14. The ostomy bag drain cap of claim 1, further comprising side seams that connect the front panel and the back panel along the sides of the pocket so that the side seams are adapted to align with the sides of the rolled drainage end.

15. A method of securing an ostomy bag drain end comprising:
rolling or folding the ostomy bad drain end into a rolled conformation in order to seal the ostomy bag drain end;
stretching the opening of an ostomy bag drain cap, the drain cap comprising a pocket configured to fit over a rolled drainage end of an ostomy bag, the pocket having a front panel made from a layered fabric and a back panel made from the layered fabric, and an opening at a top of the pocket adapted to allow the rolled drainage end to be inserted into the pocket, wherein the layered fabric has an outer layer of 4-way stretchable fabric adapted to provide elasticity and to secure the pocket around a rolled drainage end during use and a padding layer of compressible and resilient fabric inside of the outer layer of 4-way stretchable fabric, the padding layer providing body and providing cushioning around the drainage end to prevent skin irritation caused by contact with the rolled drainage end;
placing the ostomy cap around the rolled end;

releasing the stretched drain cap so that the outer layer of 4-way stretchable fabric contracts around the rolled drainage end.

16. The method of claim 15, wherein placing the ostomy cap around the rolled end further comprises aligning side seams of the pocket to abut the sides of the rolled drainage end.

17. The method of claim 15, wherein releasing the stretched drain cap further comprises releasing a stretched retention band so that the rolled drainage end is within the pocket and the retention band retains the rolled drainage end within the pocket.

18. The method of claim 15, further comprising removing the drain cap, washing the drain cap, and reusing the drain cap.

* * * * *